United States Patent [19]
Schulz et al.

[11] Patent Number: 5,190,882
[45] Date of Patent: Mar. 2, 1993

[54] METHOD FOR QUANTITATIVELY DETERMINING THE AMOUNT OF SATURATES, OLEFINS, AND AROMATICS IN A MIXTURE THEREOF

[75] Inventors: Wolfgang W. Schulz, Lebanon; Mark W. Genowitz, Phillipsburg, both of N.J.

[73] Assignee: Exxon Research and Engineering Company, Florham Park, N.J.

[21] Appl. No.: 817,217

[22] Filed: Jan. 6, 1992

Related U.S. Application Data

[63] Continuation-in-part of Ser. No. 487,579, Mar. 2, 1990, abandoned.

[51] Int. Cl.$^5$ .......................................... G01N 21/33
[52] U.S. Cl. ................................... 436/139; 436/140; 436/141; 436/142; 436/143; 436/161; 436/171; 436/173; 210/656; 73/61.53; 73/61.58
[58] Field of Search ............................... 436/139-143, 436/161, 171, 178, 173; 73/61.1 C; 210/656, 198.2

[56] References Cited

U.S. PATENT DOCUMENTS 4,341,634  7/1982  Matsushita et al. .................. 210/656
4,476,713  10/1984  Alfredson ......................... 73/61.1 C
4,988,446  1/1991  Haberman et al. .............. 436/140 X

OTHER PUBLICATIONS

Drushel, H. V. "Needs of the Chromatographer—Detectors" Journal of Chromatographic Science, vol. 21, pp. 375-384 (1983).
Campbell, R. M. "Supercritical Fluid Chromatographic Determination of Hydrocarbon Groups in Gasolines and Middle Distillate Fuels," Analytical Chemistry, vol. 60, 1988, pp. 356-362.
Norris, T. A. "Determination of Hydrocarbon Types in Petroleum Liquids by Supercritical Fluid Chromatography with Flame Ionization Detection" Analytical Chemistry, vol. 56, No. 11, 1984, pp. 1767-1769.
Lundanes, E. "Group Separation of Petroleum Using Supercritical Fluids" Journal of Chromatography, vol. 366, 1986, pp. 391-394.
Schmidt, L. "Combined Liquid Chromatography-Mass Spectrometry for Trace Analysis of Pharmaceuticals" Nuclear Instruments and Methods, vol. 198, pp. 165-167 (1982).
Brunnock, J. V. "Rapid Separation by Carbon Number and Determination of Naphthene and Paraffin Content of Saturate Petroleum Distillates up to 185° C." Analytical Chemistry, vol. 21, 1949, pp. 1377-1386.
Bornhop, D. J. "Use of Two Simultaneous Detectors in Capillary Supercritical Fluid Chromatography", Journal of Chromatography, vol. 459, 1988, pp. 193-200.
Schwartz, H. E. "Hydrocarbon Group Analysis of Gasolines with Microbore Supercritical Fluid Chromatography and Flame Ionization Detection," Journal of Chromatography, vol. 353, 1986, pp. 77-93.
TRAC, Trends in Analytical Chemistry, vol. 6, No. 1, (Jan., 1987), Cambridge GB, pp. 10-17, Schonmakers et al., "Supercritical-Fluid Chromatography—Prospects and Problems".
Analytical Chemistry, vol. 58, No. 11, (Sep., 1986) pp. 2247-2251, Campbell et al., "Supercritical Fluid Fractionation of Petroleum- and Coal-Derived Mixtures".

Primary Examiner—James C. Housel
Assistant Examiner—Jeffrey R. Snay
Attorney, Agent, or Firm—Joseph J. Dvorak

[57] ABSTRACT

A quantitative method including separating a mixture of olefins, aromatics, and saturates by supercritical fluid chromatography to obtain an eluent stream that over a first time period contains a mixture of olefins and saturates, and over a second time period contains aromatics, and passing the eluent first to an ultraviolet absorption detector (UV). Importantly, the eluent is irradiated in the UV detector at a wavelength capable of producing an ultraviolet absorbance response of olefins that is independent of specific olefins present, and preferably is substantially similar to a mass detector response for olefins. From a combination of UV and mass response, the mass of the olefins in the mixture of olefins and saturates can be determined. Thereafter, the eluent is passed to a mass detector whereby the mass of the mixture of saturates and olefins is determined and then the mass of the aromatics is determined.

9 Claims, 3 Drawing Sheets

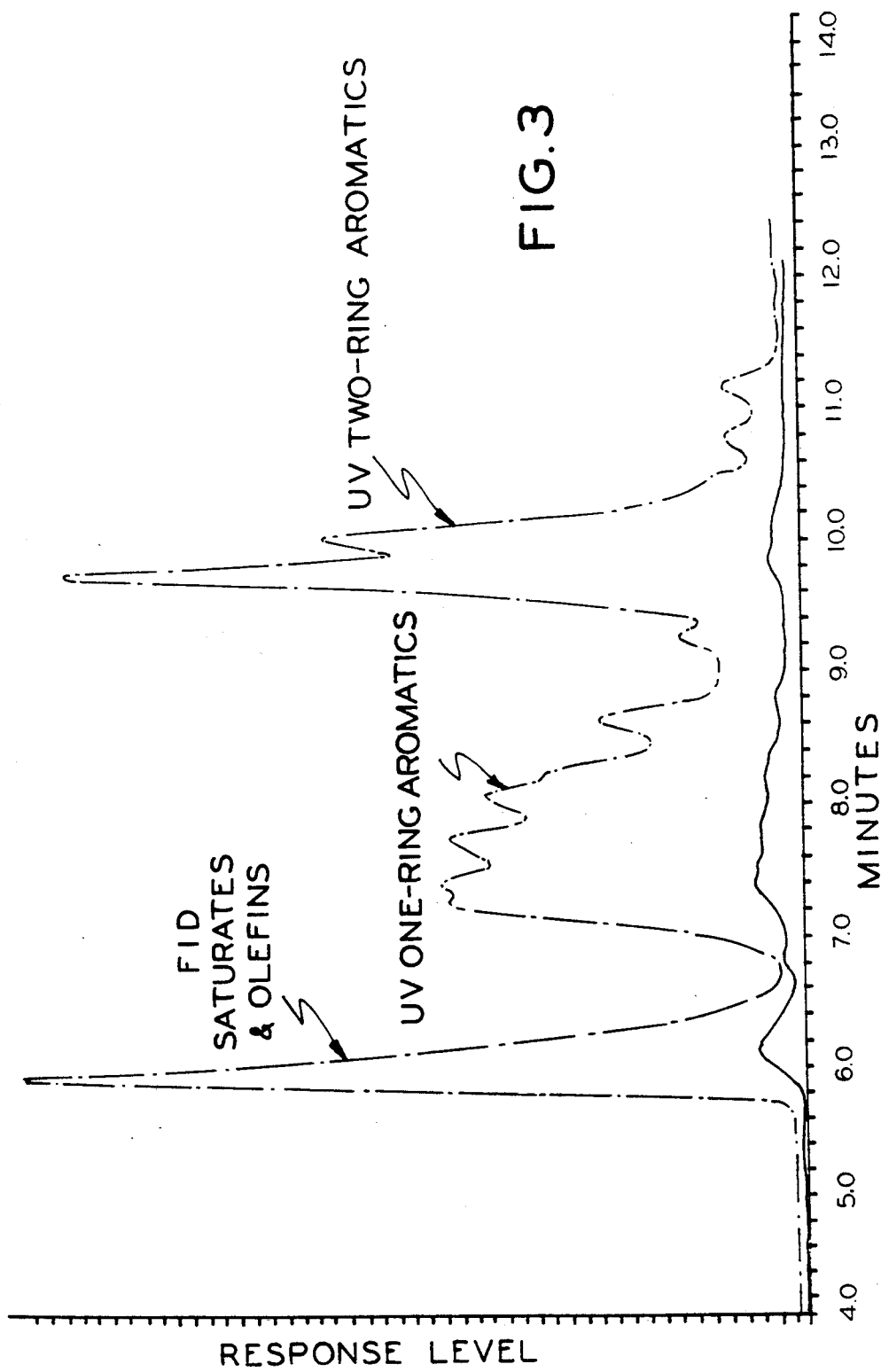

METHOD FOR QUANTITATIVELY DETERMINING THE AMOUNT OF SATURATES, OLEFINS, AND AROMATICS IN A MIXTURE THEREOF

This application is a continuation-in-part of application Ser. No. 487,579, filed Mar. 2, 1990, now abandoned.

BACKGROUND OF THE INVENTION

1. Field of the Invention

The present invention relates to a method for quantitatively determining the amount of saturates, olefins, and aromatic components in mixtures thereof.

2. Background of the Disclosure

The separation and quantitation of saturates, olefins, aromatics, and polar components present in petroleum products traditionally is performed by liquid chromatography (LC). As is known, however, liquid chromatographic methods are slow and labor intensive. Depending upon the compounds present in the mixtures, the separation efficiency may be limited and the precision achieved may be low. Therefore, in the petroleum industry the standard method for determining olefins, saturates, and aromatics in gasoline and jet fuels, for example, is the so-called fluorescence indicator adsorption method (FIA). Unfortunately, this technique fails to measure low levels of olefins and is interfered with by the presence of color and also the presence of components lighter than hexane.

With the advances that have been made in the field of chromatography and especially with the advent of supercritical fluid chromatography (SFC), attempts have been made to take advantage of these advances to develop better measurement techniques. Thus, a flame ionization detector (FID) has been used in the measurement of aromatics and saturates present in middle distillates after separation by SFC. This technique, however, is insufficient for analysis of hydrocarbon mixtures containing olefins, saturated hydrocarbons, and aromatics because olefins are not separated from saturates in SFC.

It is, therefore, an object of the present invention to provide a method whereby the quantitative amount of saturates, olefins and aromatics in a composition are easily and quickly determined.

It is a further object of the present invention to provide a method for quantitatively determining the amount of olefins, saturates, and aromatics that eliminates the need to separate the olefins and saturates in a composition.

Other objects and advantages of the present invention will be apparent to those skilled in the art, particularly upon reading the examples and disclosures herein.

SUMMARY OF THE INVENTION

The invention provides a method for quantitatively determining the amount of saturate, olefin and aromatic components in mixtures thereof.

Briefly stated, the present invention comprises separating a mixture of olefins, aromatics, and saturates by supercritical fluid chromatography to obtain an eluent stream that over a first time period contains a mixture of olefins and saturates, and over a second time period contains aromatics, and passing the eluent first to an ultraviolet absorption detector (UV). Importantly, the eluent is irradiated in the UV detector at a wavelength capable of producing an ultraviolet absorbance response of olefins that is independent of specific olefins present, and preferably is substantially similar to a mass detector response for olefins. From the combination of the UV and mass response, the mass of the olefins in the mixture of olefins and saturates can be determined. Thereafter, the eluent is passed to a mass detector whereby the mass of the mixture of saturates and olefins is determined and then the mass of the aromatics is determined.

BRIEF DESCRIPTION OF THE DRAWINGS

FIG. 3 shows the UV and FID Chromatogram for a jet fuel separated by SFC.

DETAILED DESCRIPTION

Figure 1:
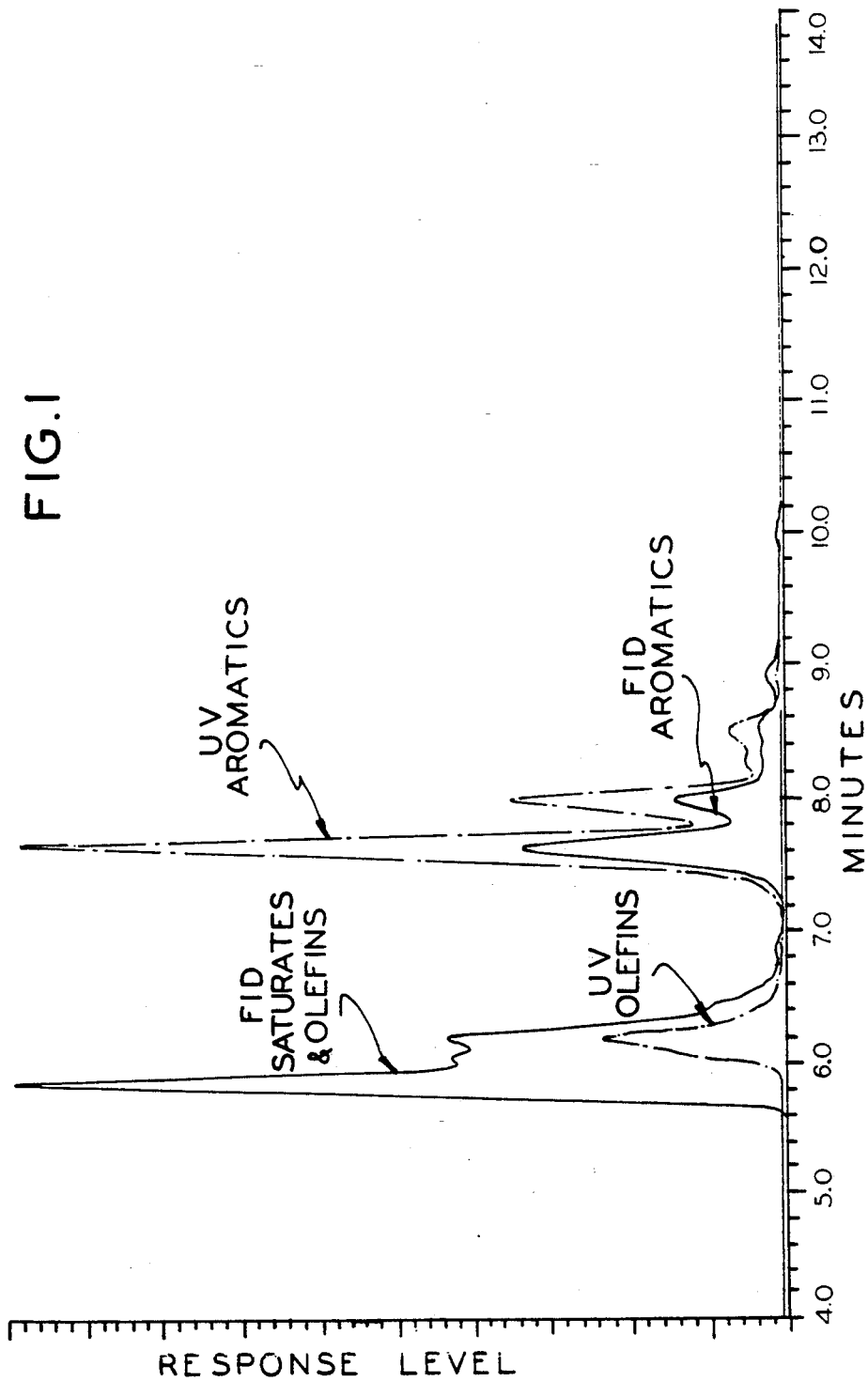
FIG. 1 is a dual chromatogram showing the separation of olefins and saturates from aromatics.

The present invention provides a method for quantitatively determining the amount of saturates, olefins, and aromatics in mixtures thereof, such as gasoline, jet fuel, middle distillates, and the like.

The method relies upon a chromatography column packed with a stationary phase that is thermally stable and capable of separating the saturate and olefin components of a sample from the aromatic components of a sample of a mixture containing saturates, olefins, and aromatics. The packing consists essentially of a porous solid support that may also have distributed thereon a non-selective stationary phase. Among the packing materials which may be used are silica, alumina, zeolites, surface modified silica, alumina and zeolites and mixtures thereof; preferred is a silica. Suitable packed columns having the above materials are commercially available.

The stationary phase of the column is used to produce a distribution of the components of the composition and later elute from the stationary phase these components depending on their particular elution order at a series of times that corresponds with the components affinity for the stationary phase. To insure highly efficient separations, it is preferred that the particle size of the stationary phase material be about 3 micrometers to about 10 micrometers and the pore diameter be from about 60 Angstroms to 300 Angstroms. Pumps may be used to provide a constant or programmed pressure throughout the chromatography column, in the range from about 100 to about 350 atmospheres.

The above described column is loaded with the saturates, olefins and aromatics of the composition by injecting a sample of the composition onto the stationary phase. The injection volume or mass is proportional to the mass or volume of the stationary phase and when expressed in volumetric units is in the range of about 1 nanoliter to about 1 microliter.

After loading the column with the sample, the sample is eluted. In carrying out the elution, a mobile phase is passed through the stationary phase having the components retained thereon.

The mobile phases suitable for carrying out the elution consist of a supercritical fluid selected from carbon dioxide, nitrous oxide, sulfur hexafluoride, xenon and mixtures thereof; preferred is carbon dioxide. The mobile phase is passed through the stationary phase under supercritical conditions. Preferably, in the case where carbon dioxide is used, these conditions consist of temperatures ranging from about 30° C. to about 50° C. and pressures ranging from about 100 atmospheres to about 350 atmospheres. However, when xenon is used as the supercritical fluid, the temperature must be at or above 17° C. The flowrate of the mobile phase through the column may be controlled by installing a porous flow restrictor in front of the mass detector. The preferred flowrates are in the range of from about 0.05 cm/sec to about 0.3 cm/sec. In general, the mobile phase will have a low viscosity and a relatively low solvent strength to enable the chromatographic column to resolve or separate the saturates and olefins from the aromatic components of the composition.

The eluent exiting the column contains the mobile phase, having passed over the stationary phase, along with saturate, olefin and aromatic components whose concentration in the eluent will vary over time. Therefore, the components are identified by their corresponding retention time, being the time at constant and given flow rate after which a component is liberated from the stationary phase in the form of an eluent. The retention time is characteristic of each component based on its relative affinity for either the mobile or stationary phase.

Once identified, the amount or concentration of these components in the eluent is measured over specific time intervals. The first time interval begins from the time the sample is injected and ends when the concentration of saturates and olefins detected in the eluent stops diminishing. The second time interval begins no sooner than the end of the first time interval and ends when the concentration of aromatics detected in the eluent stops diminishing. However, in the event where there multiple time intervals exist, the start of the second time interval is determined by injecting a model aromatic compound for elution, preferred is benzene. The end is determined by injecting a model aromatic compound for elution, preferred is pyrene.

A UV and mass detector (e.g., FID) located at the output of the chromatograph column monitor the level of saturate, olefin and aromatic components in the eluent exiting the column. The response from these detectors is essential in determining when the concentration of a given component detected in the eluent has stopped diminishing.

Heretofore, UV detectors were not used to determine the amount of olefins in a composition in which the specific olefins present may vary because different olefins are known to have different UV responses over a wide range of wavelengths. Under such conditions, it is not possible to know whether the UV response of the composition is due to the specific olefins present or their concentration. We have found, however, that olefins, for example those present in gasoline fractions, have individual ultraviolet light spectra that tend to converge at low wavelengths to give a substantially uniform ultraviolet absorbance response i.e., a response that is substantially independent of the specific olefin present. Therefore, the UV detector may be used to determine the total amount of the olefins present in a composition or mixture by tuning the detector to, i.e. irradiating the mixture with, a wavelength at which the UV absorbance response of the olefins is substantially independent of the specific olefins present in the composition. Therefore, the eluent obtained over the first time period is irradiated at a UV wavelength capable of producing a substantially uniform UV absorbance response and that response is measured. Preferably, the wavelength produces a UV response for olefins that is substantially similar to the mass detector response of the olefin compounds only. A wavelength of substantially 190 nanometers is preferred. Although the wavelength may be equal to or less than 190 nanometers.

The total mass of the components eluting from the column is determined by a mass detector which may consist of a mass spectrometer or flame ionization detector (FID); preferred is the FID. Since the separated components are consumed in the FID measurement, it is important to locate the UV detector ahead of the FID.

The signals from both detectors may be amplified upon passing through an amplifier before being recorded and integrated to provide an integral of absorbance, and first integral of mass and a second integral of mass. The amount of olefins then can be determined from the equation: $O = R/F(S+0)$ where 0 is the weight % olefins, $(S+0)$ is the weight % saturates and olefins, R is the ratio of the integral of absorbance to the first integral of mass, and F (an olefin calibration factor) is the ratio of the integral of absorbance to the first integral of mass for a known olefin.

The recorder tracing develops a profile or plot of the component distribution in the eluent as a function of time. Preferably, the recorder plot is generated from a recording potentiometer which is commercially available. The plot is in the form of time versus the concentration of the components detected in the eluent. The output of each detector is manifest by a series of signals over time separated by periods of time when no signal occurs when no components are detected. The level of the response signal for each detector before and after a peak occurs is termed the background level and represents principally the absorbance level or conductivity level of the mobile phase, also referred to as the base line. Increases in the response level from the base line are due to one or more of the components in the eluent.

The first step is to determine whether such increased level or peak is due to a component or to several components that have migrated through the chromatographic column at essentially the same time. The plot will show the time intervals along the abscissa and the response level above the base level along the ordinate. Time intervals are in minutes and begin from a data time "0" which is right after a sample of the composition is introduced to the chromatography column. There is a time lag before the detectors can detect any deviation from the steady base line response signal. Once the ultraviolet absorbance detector detects an increase in the concentration of olefins in the eluent, a sharp increase in the response from the base line signal of the detector follows. Once the concentration of olefins in the eluent stops diminishing, the signal returns toward the initial base line value of the signal. The flame ionization detector response occurs in a similar manner, however, for saturates and olefins together over a first time interval and aromatics over a second time interval.

The integrator readings provide a printed record used to calculate weight percent of the various components removed from the column based on their retention time. The integrator may be a printing electronic integrator which produces at least 6,000 counts per minute. The integrator makes measurements on the recorded area of the chromatogram at constant time intervals, preferably about every 1/15 second and converts this data into usable information which reflects the concentration of the components in the eluent. In this manner, the integrator readings provide a printed record to calculate the weight percent of the components separated at different time intervals. The integrated readings are suitable for processing in a computer controller adapted for the automatic operation of a process.

Having described the invention, the following are examples which illustrate the various workings of it. They are not intended to limit the invention in any way.

EXAMPLE 1

Eleven gasoline samples of various grades were analyzed under the analytical method of the present invention and compared to results obtained from the standard FIA test method (ASTM D-1319). To control the evaporation of the lower boiling point components in each sample, the samples were refrigerated prior to their use. The supercritical fluid chromatographic column was fitted to an injector which was water cooled. The column was inserted directly into one of the ports of the injector without the need for a connection piece. Portions of the samples were injected into the chromatograph either through total loop injection or at split time intervals which involved rapid rotation (0.02 sec) of a 60 nanoliter injection loop. The column had dimensions of 1 mm I.D., 1/16 inch O.D. and 50 cm in length. The stationary phase was a silica packing material having a particle size of 10 micrometers. The supercritical fluid mobile phase was carbon dioxide and was maintained at a flow rate of 16 cc/min, measured at the exit of the FID detector after passing through the stationary phase. The column was operated at 40° C. and at a constant pressure of 200 ATM. The ultraviolet absorbance (UV) detector was designed for operation with packed column supercritical fluid chromatography. The flow-through cell of the detector held a volume of 0.25 ml and had a path length of 2 mm and was water cooled. The upper limit of the linear response of the UV detector was sometimes exceeded if the olefin concentration in the eluent from the column varied significantly. Therefore, to ensure that the olefin UV response fell within the detector's linear response range of 1.4 absorbance units, each sample was re-run at a lower split time interval when the response signal exceeded 1.4 absorbance units. The FID required flow rates of 380 cc/min air, 30 cc/min $H_2$ and operated at a temperature of 325° C. The UV detector was placed ahead of the flow restrictor but outside of the oven with the fluid lines emerging from and returning to the oven after transversing the UV detector. The UV detector's response to olefins was calibrated with a standard olefin. The data from each detector was recorded and integrated by computer. The analysis time was 11 minutes.

According to the FID response shown in FIG. 1 a clean separation of olefins and saturates from aromatics was achievable for each gasoline sample. However, separation between olefins and saturates was not detected. The UV detector response shows that the olefins have an elution time that is at the tailing edge of the elution time for the saturates. The retention time is characteristic of each component based on its relative affinity for either the mobile or stationary phase. The saturate and olefin components are determined or considered as those components having a retention time between 5.5 to 7.0 minutes and the aromatics are determined or considered as the component having a retention time between 7.0 to 10.5 minutes. The overall time for the elution is less than about 11 minutes.

The results are compared in Table I.

Figure 2:
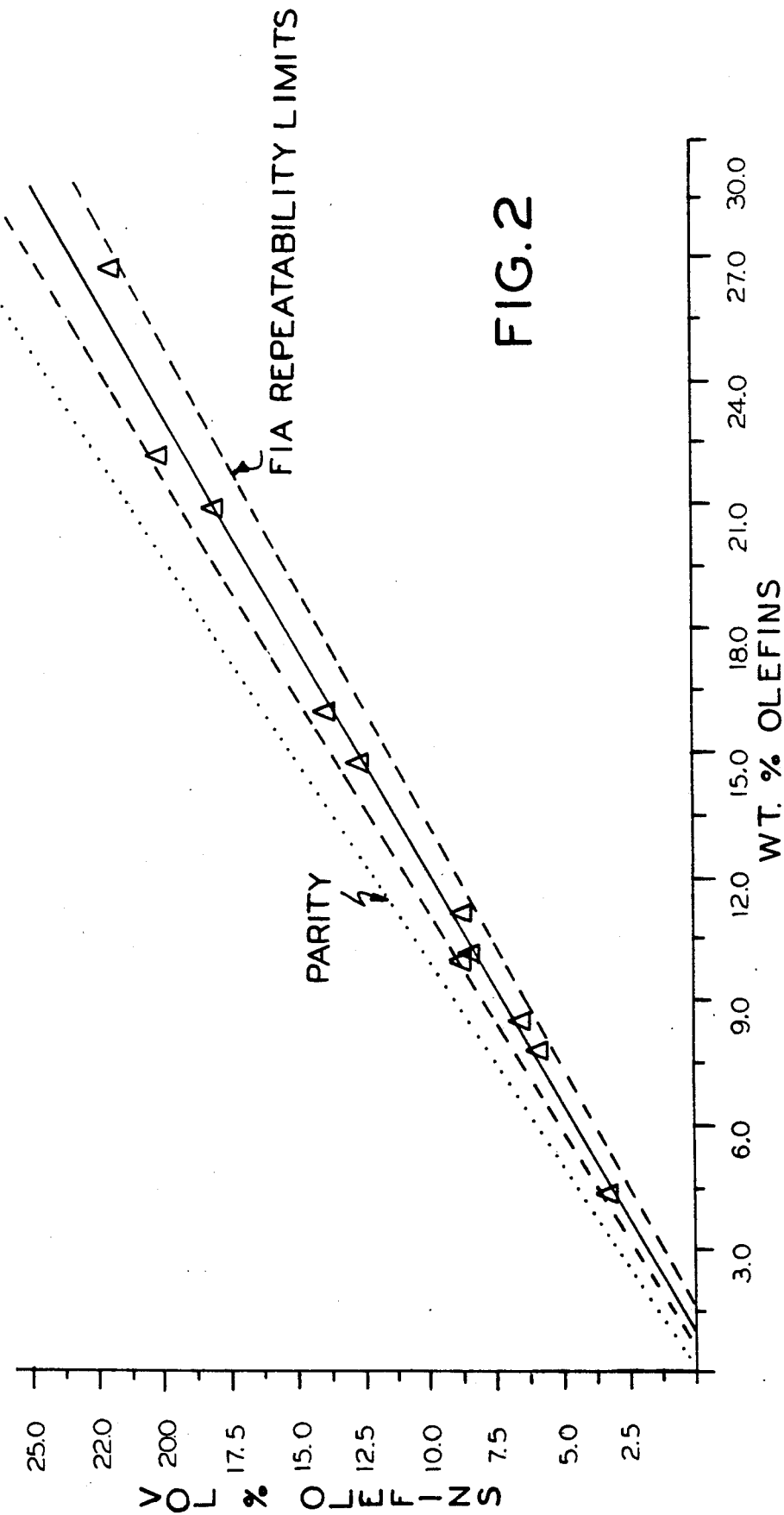
FIG. 2 is a graph showing correlation of the results of the method of the invention with the results of the standard FIA method

FIG. 2 shows that the results correlate with and are well within the repeatability limits established for the standard FIA method. This demonstrates that differences in olefin levels, as measured by the FIA method, are measured equally as well by the present analytical method. There exists a bias towards lower olefin results by the FIA method. The reason is that the densities of the various hydrocarbon types within the gasoline sample can be expected to differ. This leads to slightly different levels of results in view of the fact that FIA measures components in volume percent and the new method in weight percent

EXAMPLE 2

The method of Example 1 was carried out using a specific RR-2 reference gasoline sample. The results in terms of wt. % saturates, olefins and aromatics are listed in Table II. The results show a two sigma repeatability of 0.75 at an olefin level of 12 wt. % which compares to a value of 1.3% for the standard FIA method. This demonstrates that the short term precision for measuring olefins is better than that reported using the FIA method.

EXAMPLE 3

The method of Example 1 was carried out on a simulated gasoline blend having a 63.9 wt. % petroleum ether, 9.4 wt. % Blend II and 26.7 wt. % Aromatics (see Table III). The results showed 9.6 wt. % olefins 28 wt. % aromatics and 62.6 wt. % saturates. This shows that the present method is accurate, being capable of measuring a true level of saturates, olefins and aromatics.

EXAMPLE 4

The method of Example 1 was carried out on a jet fuel sample, the results of which are illustrated in FIG. 3. The separation of one and two ring aromatic components is quite apparent from the UV detector. Further analysis of the aromatic components can readily be quantified by the FID detector. The FIA method response for the olefins was 2.6% versus 0.4% by the present method. However, the olefin value from the FIA method is uncertain. This demonstrates that the present method is applicable to the analysis of jet fuels.

Although particular embodiments of the invention have been shown and described, it is to be understood that the scope of the invention is not limited to these embodiments, since modifications can be made by one skilled in the art.

TABLE I

A COMPARATIVE DISTRIBUTION OF HYDROCARBON COMPOUNDS IN COMMERCIAL GASOLINES BY FIA AND SFC ANALYSIS METHODS

| GASOLINE | FIA (VOL %) | | | SFC (WT %) | | |
| --- | --- | --- | --- | --- | --- | --- |
| | Saturates | Olefins | Aromatics | Saturates | Olefins | Aromatics |
| REG-UL | 53.9 | 8.4 | 37.7 | 43.3 | 10.2 | 46.5 |
| PREM-UL | 56.7 | 5.9 | 37.3 | 46.7 | 7.9 | 45.4 |
| REG-LD | 58.0 | 8.7 | 33.3 | 45.8 | 11.2 | 43.0 |

TABLE I-continued
A COMPARATIVE DISTRIBUTION OF HYDROCARBON COMPOUNDS IN COMMERCIAL GASOLINES BY FIA AND SFC ANALYSIS METHODS

| GASOLINE | FIA (VOL %) | | | SFC (WT %) | | |
| --- | --- | --- | --- | --- | --- | --- |
| | Saturates | Olefins | Aromatics | Saturates | Olefins | Aromatics |
| REG-UL | 63.6 | 12.6 | 23.8 | 56.9 | 14.8 | 28.3 |
| SUPER-UL | 52.5 | 6.5 | 41.1 | 42.5 | 8.6 | 48.9 |
| REG-UL | 47.6 | 20.1 | 32.3 | 45.1 | 22.2 | 32.7 |
| PLUS-UL | 37.3 | 21.9 | 40.8 | 36.4 | 26.8 | 36.8 |
| SUPER-UL | 42.5 | 13.8 | 41.1 | 39.4 | 16.0 | 44.6 |
| REG-UL | 58.4 | 17.9 | 23.7 | 53.1 | 20.9 | 26.0 |
| PLUS-UL | 55.9 | 3.4 | 40.7 | 46.7 | 4.4 | 48.9 |
| SUPER-UL | 58.0 | 8.7 | 33.3 | 50.4 | 10.1 | 39.5 |

REG = Regular
PREM = Premium
UL = Unleaded
LD = Leaded

TABLE II
RR-2 GASOLINE ANALYSIS BY SFC CONCENTRATIONS, WT %

| | Saturates | Olefins | Aromatics |
| --- | --- | --- | --- |
| | 56.51 | 11.55 | 31.94 |
| | 56.16 | 12.54 | 31.30 |
| | 57.46 | 12.18 | 30.36 |
| | 58.08 | 12.50 | 29.42 |
| | 59.00 | 12.70 | 28.30 |
| | 58.80 | 12.40 | 28.80 |
| | 58.86 | 12.48 | 28.66 |
| Average Value (X) | 57.84 | 12.33 | 29.83 |
| Standard Deviation ($\sigma$) | 1.07 | 0.352 | 1.30 |
| Standard Deviation (% $\sigma$) | 1.86 | 2.86 | 4.36 |

TABLE III
COMPOSITION OF SYNTHETIC HYDROCARBON BLENDS PREPARED FOR THE SFC SYSTEM

OLEFINS BLEND II
2-methyl-2-butene
4-methyl-1-pentene
2-methyl-2-pentene
cis-4-methyl-2-hexane
trans-2-heptene
2,2,4-trimethyl-2-pentene
1-octene
2-methyl-2,4-pentadiene

AROMATICS BLEND
1,2,4-trimethylbenzene
xylenes
toluene

| GASOLINE BLEND, WT. % | ACTUAL | FOUND |
| --- | --- | --- |
| Petroleum ether | 63.9 | 62.6 |
| Olefin Blend II | 9.4 | 9.6 |
| Aromatic Blend | 26.7 | 28.0 |

What is claimed is:

1. A method for determining the concentration of saturates, olefins and aromatics in a composition comprising:
   (a) contacting a chromatographic stationary phase with a sample of the composition for a time sufficient to load said saturates, olefins and aromatics onto said stationary phase;
   (b) separating said saturates, olefins and aromatics, loaded on said stationary phase, by passing a mobile phase, under super critical conditions, through said stationary phase in a sufficient concentration and for a time sufficient to obtain an eluent wherein the concentration of saturates, olefins and aromatics in said eluent varies over time such that the concentration of saturates and olefins in said eluent obtained over a first time interval is substantially higher than over a second time interval, said second time interval being a time interval at least after said first time interval and the concentration of aromatics in said eluent obtained over said second time interval is substantially higher than over said first time interval;
   (c) passing said eluent through an ultraviolet absorption detector and irradiating said eluent with ultraviolet light at a wavelength capable of producing a uniform ultraviolet absorbance response for said olefins that is independent of the specific olefins present and measuring said ultraviolet absorbance response over said first time interval;
   (d) passing said eluent through a mass detector capable of producing a mass response to saturates and olefins in said eluent obtained over said first time interval and capable of producing a mass response to said aromatics in said eluent obtained over said second time interval and measuring said mass response over said first time interval and said second time interval;
   (e) determining the concentration of saturates, olefins and aromatics from said measurements obtained in steps (c) and (d).

2. The method of claim 1 wherein said measurements generated by said ultraviolet absorption detector are stored and integrated over said first time interval to obtain an integral of absorbance and said measurements generated by said mass detector are stored and integrated over said first and second time intervals to obtain a first integral of mass and a second integral of mass, respectively, wherein:
   (i) the concentration of aromatics expressed as weight percent of aromatics is represented by the ratio of said second integral of mass to the sum of said first and said second integral of mass;
   (ii) the concentration of saturates and olefins expressed as the weight percent saturates and olefins is represented by the ratio of said first integral of mass to the sum of said first and second integral of mass; and
   (iii) the concentration of olefins expressed as the weight percent olefins is determined from the equation: $0 = R/F (S + 0)$ where 0 is the weight percent olefins; $(S + 0)$ is the weight percent saturates and olefins, R is the ratio of said integral of UV absorbance to the said first integral of mass; F, an olefin calibration factor, is the ratio of said integral of UV absorbance to a first integral of mass for a known olefin;

(iv) the concentration of saturates expressed as the weight percent saturates is determined by subtracting the weight percent of olefins obtained in (iii) from the weight percent of saturates and olefins obtained in (ii).

3. The method of claim 2 wherein the wavelength capable of producing a uniform ultraviolet absorbance response for olefins is substantially equal to or less than 190 nanometers.

4. The method of claim 3 wherein the stationary phase is selected from the group consisting of silica, alumina, zeolites and mixtures thereof.

5. The method of claim 4 wherein the stationary phase is silica.

6. The method of claim 4 wherein the mobile phase is selected from the group consisting of carbon dioxide, nitrous oxide, sulfur hexafluoride, xenon and mixtures thereof.

7. The method of claim 6 wherein the mobile phase is carbon dioxide.

8. The method of claim 3 wherein said mass detector is either a flame ionization detector (FID) or a mass spectrometer detector.

9. The method of claim 8 wherein said mass detector is a flame ionization detector.

* * * * *